(12) United States Patent
Ewart et al.

(10) Patent No.: US 10,918,623 B2
(45) Date of Patent: Feb. 16, 2021

(54) METHODS OF TREATING INFLUENZA

(71) Applicant: Biotron Limited, Sydney (AU)

(72) Inventors: Gary Ewart, Hackett (AU); Carolyn Luscombe, Sydney (AU)

(73) Assignee: Biotron Limited, Sydney (AU)

( * ) Notice: Subject to any disclaimer, the term of this patent is extended or adjusted under 35 U.S.C. 154(b) by 29 days.

(21) Appl. No.: 16/483,958

(22) PCT Filed: Feb. 7, 2018

(86) PCT No.: PCT/AU2018/050085
§ 371 (c)(1),
(2) Date: Aug. 6, 2019

(87) PCT Pub. No.: WO2018/145148
PCT Pub. Date: Aug. 16, 2018

(65) Prior Publication Data
US 2020/0093796 A1 Mar. 26, 2020

(30) Foreign Application Priority Data

Feb. 8, 2017 (AU) ................. 2017900385

(51) Int. Cl.
| *A61K 31/415* | (2006.01) |
| *A61P 31/16* | (2006.01) |
| *A61K 9/00* | (2006.01) |
| *A61K 31/196* | (2006.01) |
| *A61K 31/215* | (2006.01) |
| *A61K 31/351* | (2006.01) |

(52) U.S. Cl.
CPC .......... *A61K 31/415* (2013.01); *A61K 9/0053* (2013.01); *A61K 31/196* (2013.01); *A61K 31/215* (2013.01); *A61K 31/351* (2013.01); *A61P 31/16* (2018.01)

(58) Field of Classification Search
CPC ............ A61K 2300/00; A61K 31/196; A61K 31/215; A61K 31/415; A61K 31/7012; A61K 31/351; A61K 45/06; A61K 9/0053; A61P 31/16
See application file for complete search history.

(56) References Cited

U.S. PATENT DOCUMENTS

| 2014/0066487 A1 | 3/2014 | Ewart et al. |
| 2016/0376231 A1 | 12/2016 | Ewart et al. |

OTHER PUBLICATIONS

Jalily et al., "Mechanisms of Action of Novel Influenza A/M2 Viroporin Inhibitors Derived from Hexamethylene Amiloride," *Molecular Pharmacology*, vol. 90, pp. 80-95, 2016.

*Primary Examiner* — Savitha M Rao
(74) *Attorney, Agent, or Firm* — Klarquist Sparkman, LLP

(57) ABSTRACT

The present invention relates to the treatment or prevention of influenza virus infection. In particular, the present invention relates to the use of N-carbamimidoyl-5-(1-methyl-1H-pyrazol-4-yl)-2-naphthamide, or a pharmaceutically acceptable salt thereof, in the treatment or prevention of influenza virus infection.

15 Claims, 3 Drawing Sheets

METHODS OF TREATING INFLUENZA

FIELD OF THE INVENTION

Cross Reference to Related Applications

This is the § 371 U.S. National Stage of International Application No. PCT/AU2018/050085, filed Feb. 7, 2018, which was published in English under PCT Article 21(2), which in turn claims priority from Australian Provisional Patent Application No. 2017900385, filed Feb. 8, 2017, the contents of which are incorporated in their entirety herein.

The present invention relates to the treatment or prevention of influenza virus infection. In particular, the present invention relates to antiviral compounds and their use in the treatment or prevention of influenza virus infection.

BACKGROUND OF THE INVENTION

Any discussion of the prior art throughout the specification should in no way be considered as an admission that such prior art is widely known or forms part of common general knowledge in the field.

Influenza is one of the few common infectious diseases poorly controlled by modern medicine. The burden of Influenza is heavy, with the World Health Organisation estimating 5-10% of adults and 20-30% of children in the global population (3-5 million people) are affected by annual epidemics, causing between 250,000-500,000 deaths per year.

Symptoms of influenza infection can be mild to severe. The most common symptoms include: a high fever, runny nose, sore throat, muscle pains, headache, coughing, and fatigue. Complications associated with flu include pneumonia, bronchitis, sinus infections and ear infections. Other possible serious complications triggered by flu can include inflammation of the heart, brain or muscle, and multi-organ failure. Infection of the respiratory tract can trigger an extreme inflammatory response in the body and can lead to sepsis. Flu can also make chronic medical problems worse. For example, people with asthma may experience asthma attacks while they have the flu, and people with chronic heart disease may experience a worsening of this condition triggered by flu.

Influenza is caused by viruses of the family Orthomyxoviridae, and there are three types of influenza viruses that affect people, called Type A, Type B, and Type C. These influenza viruses generally lead to similar symptoms but the virus types are unrelated antigenically, so that infection with one type confers no immunity against the other. Influenza A and B viruses cause seasonal epidemics almost every winter. The emergence of a new and very different influenza A virus to infect people can cause an influenza pandemic. Influenza type C infections generally cause a mild respiratory illness and are not thought to cause epidemics.

Influenza A viruses can be broken down into different subtypes according to genetic variations of two different viral surface proteins: hemagglutinin (HA/H in subtype) and neuraminidase (NA/N in subtype). There are 16 different HAs and 9 NAs which are distinguishable serologically. Influenza B viruses are not divided into subtypes, but can be broken down into lineages. Currently circulating influenza B viruses belong to one of two lineages: B/Yamagata and B/Victoria. Further variation exists and specific influenza strain isolates are identified by a standard nomenclature specifying virus type, host of origin, geographical origin, sequential number of isolation, year of isolation, and for influenza A the HA and NA subtype.

When a new strain of influenza virus appears, human populations have little native resistance and existing influenza vaccines often have limited efficacy as they are typically active against specific influenza A and B viruses that differ from those in the emerging strain. This phenomenon has led to epidemics that occur regularly. Moreover, influenza viruses undergo a gradual antigenic variation (antigenic drift) that degrades the level of immunological resistance against renewed infection. Pandemics occur every couple of decades and are due to a dramatic change (antigenic shift) in the viral HA and NA subtypes.

Anti-influenza vaccines, containing killed strains of types A and B virus currently in circulation, are available, but have only a 50 to 60% success rate in preventing infection. Standard influenza vaccines have to be redesigned each year to counter new variants of the virus. In addition, any immunity provided is short-lived. Therefore, vaccines may not prevent or limit a pandemic if the circulating strains continue to drift significantly, or another subtype emerges. Instead, antiviral agents will be critical for initial control and protection against an emerging pandemic.

Two classes of antivirals are approved for clinical use against human influenza:

Neuraminidase Inhibitors—including oseltamivir, zanamivir and peramivir.

M2 Ion-Channel Inhibitors—including amantadine and rimantadine. These medications are active against influenza A viruses, but not influenza B viruses due to structurally distinct M2 channels.

Oseltamivir has become the preferred choice of neuraminidase inhibitor for governments and organizations in their preparations for possible influenza pandemics due to its oral delivery. Stockpiles of oseltamivir were utilised during the 2009 influenza A H1N1 pandemic (Nguyen-Van-Tam et al., Clin Microbiol Infect, 2015. 21: 222-22). However, the clinical effectiveness of neuraminidase inhibitors, such as oseltamivir, is still undergoing debate. Recent reports have shown that oseltamivir reduces the time to alleviation of symptoms of influenza in adults by only 16.8 hours (Jefferson et al., Cochrane Database Syst Rev 2014; 4) and did not significantly reduce incidence of pneumonia, serious complications, hospitalizations or deaths (Nguyen-Van-Tam et al., Clin Microbiol Infect, 2015. 21: 222-225). Further, the use of oseltamivir has been shown to increase the risk of adverse effects, such as nausea, vomiting, psychiatric effects and renal events in adults and vomiting in children (Jefferson et al., Cochrane Database Syst Rev 2014; 4).

Prior to 2007, resistance to neuraminidase inhibitors among influenza viruses was generally low, ~1% (Ilyushina et al., Antivir Res, 2006. 70(3): 121-131; Stiver, CMAJ, 2003. 168(1):49-57). However, the Centres for Disease Control and Prevention reported in 2007-2008 that influenza A (H1N1) showed an emergence and worldwide spread of oseltamivir resistance. Oseltamivir-resistant influenza A viruses carrying the H275Y NA mutation emerged as a result of genetic drift and drug treatment. Since the emergence of this oseltamivir-resistant influenza virus strain there is concern that the H275Y substitution may generate a future pandemic or even become fixed in the viral genome. This brings into question the rationale for stockpiling neuraminidase inhibitors (Nguyen-Van-Tam et al., Clin Microbiol Infect, 2015. 21: 222-225), and highlights the need to continuously monitor antiviral drug susceptibilities and prioritise research for novel influenza antiviral therapeutics (Samson, et al. Antiviral Res. 2013, 98(2):174-85).

Unlike neuraminidase inhibitors, amantadine and rimantadine are inexpensive and widely available. Amantadine is a derivative of adamantane that efficiently inhibits replication of influenza A viruses (Davies et al., Science, 1964. 144: 862-863). The drug inhibits replication by directly binding to the influenza virus M2 protein in the envelope membrane and blocking its $H^+$-conductive ion channel activity that is essential for virus replication (Sugrue & Hay, Virology, 1991. 180: 617-624; Pinto et al., Cell, 1992. 69: 517-528; Schroeder et al., J Gen Virol, 1994. 75: 3477-3484). At higher concentrations amantadine also indirectly increases endosomal pH, which alters the pH-sensitive conformation of hemagglutinin reducing the release of infectious virus particles (Daniels et al., Cell, 1985. 40: 431-439; Steinhauer et al., Proc Natl Acad Sci, 1991. 88: 11525-11529).

However, amantadine and rimantadine are only effective against influenza A and drug-resistant variants can be obtained easily by culturing the virus in the presence of these agents (Cochran et al., Ann NY Acad Sci, 1965. 130(1): 432-439; Appleyard, J Gen Virol, 1977. 36: 249-255). Amantadine and rimantadine resistance develops as a result of mutations in the transmembrane region of M2 that preserve the ion channel activity while reducing the ability of the drugs to inhibit virus replication. The frequency of amantadine-resistant influenza A virus strains found circulating in the human population rose from 0.4% in 1995 to 12.3% in 2003-2004 (Bright et al., Lancet. 2005. 366, 1175-1181). In isolates from Asia, 61% of strains possessed mutations that conferred amantadine resistance.

There is a need for new antiviral therapies that are effective in the treatment of multiple subtypes and strains of influenza, in particular subtypes and strains of influenza that are resistant to current therapies.

It is an object of the present invention to overcome or ameliorate at least one of the disadvantages of the prior art, or to provide a useful alternative.

SUMMARY OF THE INVENTION

Previously, N-carbamimidoyl-5-(1-methyl-1H-pyrazol-4-yl)-2-naphthamide (BIT225) has been shown to have only limited activity against the M2 viroporin of influenza A and was not considered to be suitable for treating influenza (Jalily et al., MolPharm, 2016. 90: 80-95). However, the present application surprisingly shows that BIT225 has activity against multiple subtypes and strains of influenza virus. Importantly, BIT225 has been found to have activity against subtypes and strains that are resistant to amantadine.

The chemical structure of BIT225 is shown below:

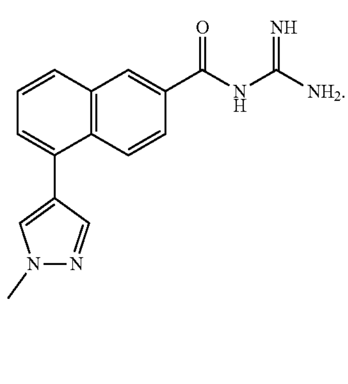 [SMILES: Cn1cc(-c2cccc3cc(C(=O)NC(=N)N)ccc23)cn1]

BIT225 may also be referred to as N-carbamimidoyl-5-(1-methylpyrazol-4-yl)naphthalene-2-carboxamide or 5-(1-methylpyrazol-4-yl)2-naphthoylguanidine.

The present invention generally relates to the use of BIT225, or a pharmaceutically acceptable salt thereof, for treating or preventing influenza, for inhibiting the replication of influenza virus, for reducing the severity, intensity, or duration of complications or symptoms associated with influenza, or for reducing the titre of influenza virus.

According to one aspect, the present invention provides a method for the treatment or prevention of influenza virus infection in a subject, the method comprising administering to the subject an effective amount of N-carbamimidoyl-5-(1-methyl-1H-pyrazol-4-yl)-2-naphthamide, or a pharmaceutically acceptable salt thereof.

According to another aspect, the present invention provides a method for inhibiting the replication of influenza virus in a subject, the method comprising administering to the subject an effective amount of N-carbamimidoyl-5-(1-methyl-1H-pyrazol-4-yl)-2-naphthamide, or a pharmaceutically acceptable salt thereof.

According to another aspect, the present invention provides a method for reducing the severity, intensity, or duration of complications or symptoms associated with influenza virus infection in a subject, the method comprising administering to the subject an effective amount of N-carbamimidoyl-5-(1-methyl-1H-pyrazol-4-yl)-2-naphthamide, or a pharmaceutically acceptable salt thereof.

According to another aspect, the present invention provides a method of reducing the titre of influenza virus in a subject, the method comprising administering to the subject an effective amount of N-carbamimidoyl-5-(1-methyl-1H-pyrazol-4-yl)-2-naphthamide, or a pharmaceutically acceptable salt thereof.

According to another aspect, the present invention provides use of N-carbamimidoyl-5-(1-methyl-1H-pyrazol-4-yl)-2-naphthamide, or a pharmaceutically acceptable salt thereof, for the manufacture of a medicament for the treatment or prevention of influenza virus infection.

According to another aspect, the present invention provides use of N-carbamimidoyl-5-(1-methyl-1H-pyrazol-4-yl)-2-naphthamide, or a pharmaceutically acceptable salt thereof, for the manufacture of a medicament for inhibiting the replication of influenza virus.

According to another aspect, the present invention provides use of N-carbamimidoyl-5-(1-methyl-1H-pyrazol-4-yl)-2-naphthamide, or a pharmaceutically acceptable salt thereof, for the manufacture of a medicament for reducing the severity, intensity, or duration of complications or symptoms associated with influenza virus infection.

According to another aspect, the present invention provides use of N-carbamimidoyl-5-(1-methyl-1H-pyrazol-4-yl)-2-naphthamide, or a pharmaceutically acceptable salt thereof, for the manufacture of a medicament for reducing the titre of influenza virus.

According to another aspect, the present invention provides a composition comprising N-carbamimidoyl-5-(1-methyl-1H-pyrazol-4-yl)-2-naphthamide, or a pharmaceutically acceptable salt thereof, for use in a method of treating or preventing influenza virus infection in a subject.

According to another aspect, the present invention provides a composition comprising N-carbamimidoyl-5-(1-methyl-1H-pyrazol-4-yl)-2-naphthamide, or a pharmaceutically acceptable salt thereof, for use in a method of inhibiting the replication of influenza virus in a subject.

According to another aspect, the present invention provides a composition comprising N-carbamimidoyl-5-(1- methyl-1H-pyrazol-4-yl)-2-naphthamide, or a pharmaceutically acceptable salt thereof, for use in a method of reducing the severity, intensity, or duration of complications or symptoms associated with influenza virus infection in a subject.

According to another aspect, the present invention provides a composition comprising N-carbamimidoyl-5-(1-methyl-1H-pyrazol-4-yl)-2-naphthamide, or a pharmaceutically acceptable salt thereof, for use in a method of reducing the titre of influenza virus in a subject.

In certain embodiments, the influenza virus is selected from influenza A virus, influenza B virus and influenza C virus.

In certain embodiments, the influenza virus is influenza A virus of any host origin (human, swine, chicken, equine etc).

In certain embodiments, the influenza A virus is selected from H1N1, H1N2, H2N2, H3N2, H3N8, H5N1, H5N2, H5N3, H5N6, H5N8, H5N9, H7N1, H7N2, H7N3, H7N4, H7N7, H7N9, H9N2, and H10N7 subtypes.

In certain embodiments, the influenza A virus is selected from H1N1, H3N2 and H5N1 subtypes.

In certain embodiments, the influenza virus is influenza B virus of any lineage.

In certain embodiments, the influenza B virus is selected from B/Yamagata and B/Victoria lineages.

In certain embodiments, the N-carbamimidoyl-5-(1-methyl-1H-pyrazol-4-yl)-2-naphthamide, or a pharmaceutically acceptable salt thereof, is administered by a route selected from oral, nasal, intravenous, intraperitoneal, inhalation and topical.

In certain embodiments, the N-carbamimidoyl-5-(1-methyl-1H-pyrazol-4-yl)-2-naphthamide, or a pharmaceutically acceptable salt thereof, is administered orally.

In certain embodiments, the N-carbamimidoyl-5-(1-methyl-1H-pyrazol-4-yl)-2-naphthamide, or a pharmaceutically acceptable salt thereof, is administered daily.

In certain embodiments, the N-carbamimidoyl-5-(1-methyl-1H-pyrazol-4-yl)-2-naphthamide, or a pharmaceutically acceptable salt thereof, is administered twice daily.

In certain embodiments, the N-carbamimidoyl-5-(1-methyl-1H-pyrazol-4-yl)-2-naphthamide, or a pharmaceutically acceptable salt thereof, is administered at a dosage of about 100 mg to about 600 mg.

In certain embodiments, the N-carbamimidoyl-5-(1-methyl-1H-pyrazol-4-yl)-2-naphthamide, or a pharmaceutically acceptable salt thereof, is administered orally and is administered at a dosage of about 600 mg.

In certain embodiments, the N-carbamimidoyl-5-(1-methyl-1H-pyrazol-4-yl)-2-naphthamide, or a pharmaceutically acceptable salt thereof, is administered orally and is administered at a dosage of about 200 mg.

In certain embodiments, the N-carbamimidoyl-5-(1-methyl-1H-pyrazol-4-yl)-2-naphthamide, or a pharmaceutically acceptable salt thereof, is administered orally and is administered at a dosage of about 100 mg.

In certain embodiments, the N-carbamimidoyl-5-(1-methyl-1H-pyrazol-4-yl)-2-naphthamide, or a pharmaceutically acceptable salt thereof, is administered orally and is administered daily.

In certain embodiments, the N-carbamimidoyl-5-(1-methyl-1H-pyrazol-4-yl)-2-naphthamide, or a pharmaceutically acceptable salt thereof, is administered orally and is administered twice daily.

In certain embodiments, the N-carbamimidoyl-5-(1-methyl-1H-pyrazol-4-yl)-2-naphthamide, or a pharmaceutically acceptable salt thereof, is administered orally, once daily at a dosage of about 200 mg.

In certain embodiments, the N-carbamimidoyl-5-(1-methyl-1H-pyrazol-4-yl)-2-naphthamide, or a pharmaceutically acceptable salt thereof, is administered orally, twice daily at a dosage of about 200 mg.

In certain embodiments, the N-carbamimidoyl-5-(1-methyl-1H-pyrazol-4-yl)-2-naphthamide, or a pharmaceutically acceptable salt thereof, is administered orally, once daily at a dosage of about 100 mg.

In certain embodiments, the N-carbamimidoyl-5-(1-methyl-1H-pyrazol-4-yl)-2-naphthamide, or a pharmaceutically acceptable salt thereof, is administered orally, twice daily at a dosage of about 100 mg.

In certain embodiments, the N-carbamimidoyl-5-(1-methyl-1H-pyrazol-4-yl)-2-naphthamide, or a pharmaceutically acceptable salt thereof, is administered in combination with one or more additional antiviral agents.

In certain embodiments, the additional antiviral agents are selected from zanamivir, oseltamivir and peramivir.

DEFINITIONS

Figure 1:
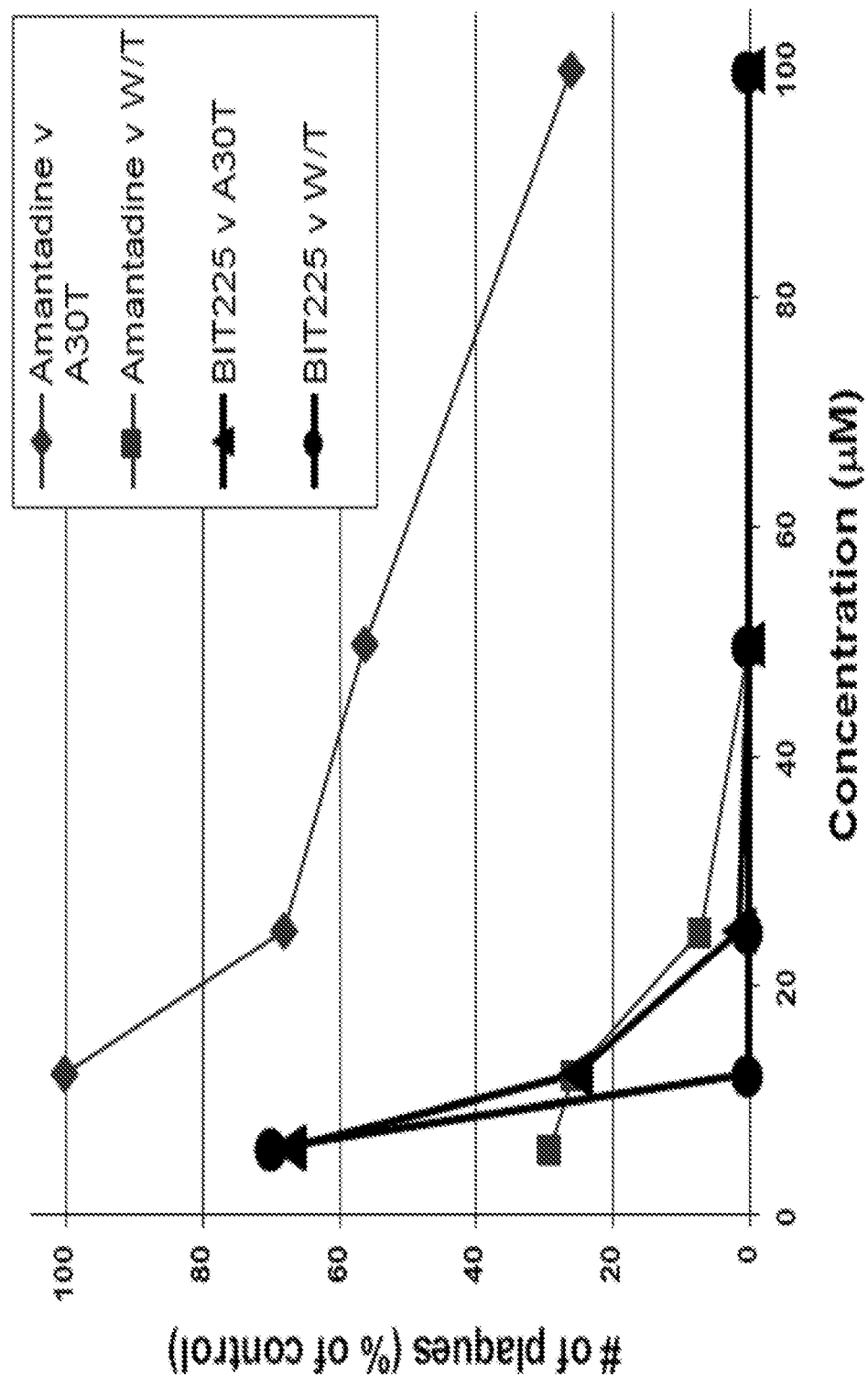
FIG. 1: This figure demonstrates the $EC_{50}$ for BIT225, which was approximately 10 µM against both the wild-type and A30T mutant viruses, with respective $EC_{90}$ values of 12 µM and 18 µM. This is in stark contrast to the large shift in drug sensitivity to amantadine caused by the A30T mutation in M2.

In describing and claiming the present invention, the following terminology has been used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

In the context of the present invention, the words "comprise", "comprising" and the like are to be construed in their inclusive, as opposed to their exclusive, sense, that is in the sense of "including, but not limited to".

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "influenza virus" as used herein, refers to an RNA virus of the Orthomyxoviridae family, including influenza A, influenza B, and influenza C, and mutants thereof. Influenza A viruses contemplated herein include those viruses that have two antigenic glycosylated enzymes on their surface: neuraminidase and hemagglutinin. Various subtypes of influenza A virus that can be treated using the materials and methods of the subject invention include, but are not limited to, H1N1, H1N2, H2N2, H3N2, H3N8, H5N1, H5N2, H5N3, H5N6, H5N8, H5N9, H7N1, H7N2, H7N3, H7N4, H7N7, H7N9, H9N2, and H10N7. Influenza B viruses include, but are not limited to, B/Yamagata and B/Victoria lineages.

As used herein, the term "influenza" or "flu" refers to an infectious disease caused by an influenza virus.

The term "symptom(s)" as used herein, refers to signs or indications that a subject is suffering from a specific condition or disease. For example, symptoms associated with an influenza infection, as used herein, refer to signs or indications that a subject is infected with an influenza virus. Influenza-related symptoms contemplated herein include, but are not limited to, fever, headache, exhaustion/fatigue, muscular aches, sore joints, irritated watering eyes, malaise, nausea and/or vomiting, shaking, chills, chest pain, sneezing and respiratory symptoms (i.e., inflamed respiratory mucous membranes, substernal burning, nasal discharge, scratchy/sore throat, dry cough, loss of smell).

Symptoms associated with an influenza infection can start within 24 to 48 hours after infection and can begin suddenly. Chills or a chilly sensation are often the first indication of influenza. Fever is common during the first few days, and the temperature may rise to 39° C. In many instances, subjects feel sufficiently ill to remain in bed for days; subjects often experience aches and pains throughout the body, most pronounced in the back and legs.

As used herein, the term "complication(s)" refers to a pathological process or event occurring during a disease or condition that is not an essential part of the disease or condition; where it may result from the disease/condition or from independent causes. Accordingly, the term complication(s) refers to medical/clinical problems that are observed in subjects diagnosed with an influenza infection. One complication of an influenza infection is that the influenza infection can make chronic health problems worse. For example, complications associated with an influenza infection include, without limitation, encephalitis, bronchitis, tracheitis, myositis rhinitis, sinusitis, asthma, bacterial infections (i.e., streptococcus aureus bacterial infection, Haemophilus influenzae bacterial infection, staphylococcal pneumonia bacterial infection), cardiac complications (i.e., atrial fibrillation, myocarditis, pericarditis), Reye's syndrome, neurologic complications (i.e., confusion, convulsions, psychosis, neuritis, Guillain-Barre syndrome, coma, transverse myelitis, encephalitis, encephalomyelitis), toxic shock syndrome, myositis, myoglobinuria, and renal failure, croup, otitis media, viral infections (i.e., viral pneumonia), pulmonary fibrosis, obliterative bronchiolitis, bronchiectasis, exacerbations of asthma, exacerbations of chronic obstructive pulmonary disease, lung abscess, empyema, pulmonary aspergillosis, myositis and myoglobinaemia, heart failure, early and late fetal deaths in pregnant women, increased perinatal mortality in pregnant women, and congenital abnormalities in birth.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of an influenza virus infection, disease or symptom associated therewith; (ii) reduce the duration of an influenza virus infection, disease or symptom associated therewith; (iii) prevent the progression of an influenza virus infection, disease or symptom associated therewith; (iv) cause regression of an influenza virus infection, disease or symptom associated therewith; (v) prevent the development or onset of an influenza virus infection, disease or symptom associated therewith; (vi) prevent the recurrence of an influenza virus infection, disease or symptom associated therewith; (vii) reduce or prevent the spread of an influenza virus from one cell to another cell, one tissue to another tissue, or one organ to another organ; (ix) prevent or reduce the spread of an influenza virus from one subject to another subject; (x) reduce organ failure associated with an influenza virus infection; (xi) reduce hospitalization of a subject; (xii) reduce hospitalization length; (xiii) increase the survival of a subject with an influenza virus infection or disease associated therewith; (xiv) eliminate an influenza virus infection or disease associated therewith; (xv) inhibit or reduce influenza virus replication; (xvi) inhibit or reduce the entry of an influenza virus into a host cell(s); (xviii) inhibit or reduce replication of the influenza virus genome; (xix) inhibit or reduce synthesis of influenza virus proteins; (xx) inhibit or reduce assembly of influenza virus particles; (xxi) inhibit or reduce release of influenza virus particles from a host cell(s); (xxii) reduce influenza virus titre; and/or (xxiii) enhance or improve the prophylactic or therapeutic effect(s) of another therapy.

In certain embodiments, the effective amount does not result in complete protection from an influenza virus disease, but results in a lower titre or reduced number of influenza viruses compared to an untreated subject. In certain embodiments, the effective amount results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titre of influenza virus relative to an untreated subject. In some embodiments, the effective amount results in a reduction in titre/volume or weight of sample of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titre, number or total burden of influenza virus include, but are not limited to, less severe symptoms of the infection, fewer symptoms of the infection and a reduction in the length of the disease associated with the infection.

"Concurrent administration", "concurrently administering", "co-administration", "co-administered" and the like as used herein, includes administering BIT225, or a pharmaceutically acceptable salt thereof, and one or more additional viral therapeutics together in a manner suitable for the treatment of an influenza infection or for the treatment of influenza infection-related symptoms/complications. As contemplated herein, concurrent administration includes providing to a subject BIT225, or a pharmaceutically acceptable salt thereof, and one or more additional viral therapeutics as separate compounds, such as, for example, separate pharmaceutical compositions administered consecutively, simultaneously, or at different times. Preferably, if BIT225, or a pharmaceutically acceptable salt thereof, and one or more additional viral therapeutic are administered separately, they are not administered so distant in time from each other that BIT225, or a pharmaceutically acceptable salt thereof, and the one or more additional viral therapeutic cannot interact. BIT225, or a pharmaceutically acceptable salt thereof, and one or more additional viral therapeutic may be administered in any order. In one embodiment, BIT225, or a pharmaceutically acceptable salt thereof, can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration the one or more additional viral therapeutics to a subject. According to the subject invention, concurrent administration also encompasses providing one or more additional viral therapeutics in admixture with BIT225, or a pharmaceutically acceptable salt thereof, such as in a pharmaceutical composition.

An additional viral therapeutic of the invention includes vaccinations or antiviral medications such as a neuraminidase or hemagglutinin inhibitor or medications that modulate the immune system or host cell factors. Contemplated viral therapeutics for use in accordance with the subject invention include, but are not limited to, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, and valaciclovir.

In related embodiments, a subject diagnosed with an influenza infection, BIT225, or a pharmaceutically acceptable salt thereof, may be concurrently administered with other therapeutics useful in the treatment of symptoms associated with an influenza infection. For example, antitussives, mucolytics, expectorants, antipyretics, analgesics, or nasal decongestants can be concurrently administered with BIT225, or a pharmaceutically acceptable salt thereof, to a subject diagnosed with an influenza infection.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is dormant.

As used herein, the expression "treating influenza virus infection" means improving, reducing, or alleviating at least one symptom or biological consequence of influenza virus infection in a subject, and/or reducing or decreasing influenza virus titer, load, replication or proliferation in a subject following exposure to an influenza virus. The expression "treating influenza virus infection" also includes shortening the time period during which a subject exhibits at least one symptom or biological consequence of influenza virus infection after being infected by influenza virus. Methods for treating influenza virus infection, according to the present invention, comprise administering a pharmaceutical composition of the present invention to a subject after the subject is infected with an influenza virus and/or after the subject exhibits or is diagnosed with one or more symptoms or biological consequences of influenza virus infection.

As used herein, the expression "preventing influenza virus infection" means preventing at least one symptom or biological consequence of influenza virus infection in a subject, and/or inhibiting or attenuating the extent to which influenza virus is capable of entering, spreading, and/or propagating within/among cells of an animal body. The expression "preventing influenza virus infection" also includes decreasing the susceptibility of a subject to at least one symptom or biological consequence of influenza virus infection. Methods for preventing influenza virus infection (i.e., prophylaxis) comprise administering a pharmaceutical composition of the present invention to a subject before the subject is infected with an influenza virus and/or before the subject exhibits one or more symptoms or biological consequences of influenza virus infection. Methods for preventing influenza virus infection may include administering a pharmaceutical composition of the present invention to a subject at a particular time period or season of the year (e.g., during the 1-2 month period just prior to the time at which peak numbers of individuals are typically found to experience influenza virus infection), or before the subject travels to or is exposed to an environment with high frequencies of influenza virus infection, and/or before the subject is exposed to other subjects who are infected with influenza virus.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

As used herein, the term "titre" in the context of a virus refers to the number of viral particles present in a given volume of blood or other biological fluid or tissue or organ weight. The terms "viral load" and "viral burden" may also be used.

As used herein, the term "subject" is used to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant.

Routes of administration include, but are not limited to, intravenous, intraperitoneal, subcutaneous, intracranial, intradermal, intramuscular, intraocular, intrathecal, intracerebral, intranasal, transmucosal, or by infusion orally, rectally, via iv drip, patch and implant. Oral routes are particularly preferred.

Compositions suitable for injectable use include sterile aqueous solutions (where water soluble) and sterile powders for the extemporaneous preparation of sterile injectable solutions. The carrier can be a solvent or dispersion medium containing, for example, water, ethanol, polyol (for example, glycerol, propylene glycol and liquid polyethylene glycol, and the like), suitable mixtures thereof and vegetable oils. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by, for example, filter sterilization or sterilization by other appropriate means. Dispersions are also contemplated and these may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

When the active ingredients are suitably protected, they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.01% by weight, more preferably 0.1% by weight, even more preferably 1% by weight of active compound. The percentage of the compositions and preparations may, of course, be varied and may conveniently be between about 1 to about 99%, more preferably about 2 to about 90%, even more preferably about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 ng and 2000 mg of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels. In such forms, components may be added or modified to assist in penetration of the surface barrier.

Procedures for the preparation of dosage unit forms and topical preparations are readily available to those skilled in the art from texts such as Pharmaceutical Handbook, 19$^{th}$ edition (Edited by Ainley Wade), The Pharmaceutical Press London; CRC Handbook of Chemistry and Physics (edited by Robert C. Weast), CRC Press Inc.; Goodman and Gilman's The Pharmacological basis of Therapeutics, 9$^{th}$ edition, McGraw Hill; Remington: The Science and Practice of Pharmacy, 19$^{th}$ edition (edited by Joseph P. Remington and Alfonso R. Gennaro), Mack Publishing Co.

The term "pharmaceutically acceptable salt," as used herein, refers to any salt of BIT225 that is pharmaceutically acceptable and does not greatly reduce or inhibit the activity BIT225. Suitable examples include acid addition salts, with an organic or inorganic acid such as acetate, tartrate, trifluoroacetate, lactate, maleate, fumarate, citrate, methane, sulfonate, sulfate, phosphate, nitrate, or chloride.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding.

Effective amounts contemplated by the present invention will vary depending on the severity of the condition and the health and age of the recipient. In general terms, effective amounts may vary from 0.01 ng/kg body weight to about 100 mg/kg body weight. Effective amounts include about 100 mg to about 600 mg, in particular about 100 mg, about 150 mg, about 200 mg, about 250 mg, about 300 mg, about 350 mg, about 400 mg, about 450 mg, about 500 mg, about 550 mg, or about 600 mg.

Other than in the operating examples, or where otherwise indicated, all numbers expressing quantities of ingredients or reaction conditions used herein are to be understood as modified in all instances by the term "about".

The recitation of a numerical range using endpoints includes all numbers subsumed within that range (e.g., 1 to 5 includes 1, 1.5, 2, 2.75, 3, 3.80, 4, 5, etc.).

Preferred Embodiment of the Invention

Although the invention has been described with reference to certain embodiments detailed herein, other embodiments can achieve the same or similar results. Variations and modifications of the invention will be obvious to those skilled in the art and the invention is intended to cover all such modifications and equivalents.

The present application is based on the surprising finding that BIT225 has activity against multiple subtypes and strains of influenza virus. Importantly, BIT225 has been found to have activity against subtypes and strains that are resistant to Amantadine.

The present invention provides methods and compositions (such as pharmaceutical compositions) for treating or preventing influenza.

The present invention provides materials and methods for preventing and/or treating viral infections. Specifically, the subject invention provides materials and methods for preventing influenza infection; treating/ameliorating symptoms associated with influenza infections; and/or preventing/delaying the onset of complications associated with influenza infections.

The present invention provides a method for the treatment or prevention of influenza virus infection in a subject, the method comprising administering to the subject an effective amount of BIT225, or a pharmaceutically acceptable salt thereof.

The present invention also provides a method for inhibiting the replication of influenza virus in a subject, the method comprising administering to the subject an effective amount BIT225, or a pharmaceutically acceptable salt thereof.

The present invention further provides a method for reducing the severity, intensity, or duration of complications or symptoms associated with influenza virus infection in a subject, the method comprising administering to the subject an effective amount BIT225, or a pharmaceutically acceptable salt thereof.

The invention further provides a method of reducing the titre of influenza virus in a subject, the method comprising administering to the subject an effective amount of BIT225, or a pharmaceutically acceptable salt thereof.

The present invention is further described by the following non-limiting examples.

Examples

Production of BIT225

A mixture of 5-bromo-2-naphthoic acid (2.12 g, 8.44 mmol), 1-methyl-4-(4,4,5,5-tetramethyl-1,3,2-dioxaborolan-2-yl)-1H-pyrazole (1.84 g, 8.86 mmol), and tetrakis(triphenylphosphine)palladium(0) (502 mg, 0.435 mmol) in a 250 mL round bottomed flask was evacuated and purged with nitrogen (in three cycles). Acetonitrile (40 mL) and 2M aqueous sodium carbonate (10 mL) were added to the mixture via syringe, and the mixture was heated under reflux under nitrogen for 22 hours. The reaction mixture was allowed to cool before the addition of 1M aqueous hydrochloric acid (30 mL) and it was then extracted with ethyl acetate (3×50 mL). The combined organic layers were dried (MgSO$_4$), filtered, and concentrated in vacuo to provide a crude product (2.98 g after air drying). This crude material was dissolved in hot ethanol (150 mL) and filtered while hot to remove a yellow impurity (120 mg). The filtrate was concentrated in vacuo and the residue was recrystallised from dichloromethane (30 mL) to provide 5-(1-methyl-1H-pyrazol-4-yl)-2-naphthoic acid as a white solid (724 mg, 34%). A second crop of 5-(1-methyl-1H-pyrazol-4-yl)-2-naphthoic acid (527 mg, 25%) was obtained from the concentrated mother liquors by recrystallisation from dichloromethane (20 mL).

Oxalyl chloride (1.1 mL, 13 mmol) was added to the solution of 5-(1-methyl-1H-pyrazol-4-yl)-2-naphthoic acid (1.19 g, 4.71 mmol) in anhydrous dichloromethane (200 mL (which was added in portions during the reaction to effect dissolution)) containing dimethylformamide (2 drops) under nitrogen and the mixture was stirred at room temperature for 4.25 hours. The reaction mixture was then heated for 1 hour at 40° C., before being concentrated under reduced pressure. The resulting crude acid chloride was suspended in anhydrous tetrahydrofuran (50 mL) and this mixture was added dropwise to a solution of guanidine hydrochloride (2.09 g, 21.9 mmol) in 2M aqueous sodium hydroxide (15 mL, 30 mmol) and the reaction mixture was then stirred for 30 minutes. The organic phase was separated, and the aqueous phase was extracted with chloroform (3×30 mL) followed by ethyl acetate (3×30 mL). The combined organic extracts were washed sequentially with 1M aqueous sodium hydroxide (60 mL) and water (40 mL), then dried (Na$_2$SO$_4$) and concentrated in vacuo to give a glassy solid (1.45 g after drying under high vacuum). This solid was dissolved in dichloromethane which was then allowed to evaporate slowly to give BIT225 as a yellow solid (1.15 g, 83%).

Virus Strains

The activity of BIT225 was measured against the following viral strains:
Influenza A/New Caledonia/20/99 (H1N1). Recent clinical isolate used in latest vaccine (CDC);
Influenza A/Panama/2007/99 (H3N2). Recent clinical isolate used in latest vaccine (CDC);
Influenza B/Hong Kong/330/02. Recent clinical isolate used in latest vaccine (CDC);
Influenza A/NWS/33 (H1N1). A well-recognized laboratory strain (KW. Cochran, Univ. Michigan).

All viral strains were tested in the presence of trypsin, although in certain studies the A/NWS/33 virus was used without trypsin.

Assay of Antiviral Activity:

Rapid Screening Assay

The standard cytopathic effect (CPE) assay uses an 18 hour monolayer (80-100% confluent) of the appropriate cells, medium is removed and each of the concentrations of test compound or placebo added, followed within 15 minutes by virus or virus diluent. Two wells are used for each concentration of compound for both antiviral and cytotoxicity testing. The plate is sealed and incubated for the standard time period required to induce near-maximal viral CPE. The plate is then stained with neutral red by the method described below and the percentage of uptake indicating viable cells read on a microplate autoreader at dual wavelengths of 405 and 540 nm, with the difference taken to eliminate background. An approximated virus-inhibitory concentration, 50% endpoint (EC$_{50}$) and cell-inhibitory concentration, 50% endpoint (CC$_{50}$) are determined from which a general selectivity index is calculated: $SI=(CC_{50})/(EC_{50})$. An SI of 3 or greater triggers confirmatory testing.

Inhibition of Viral Cytopathic Effect (CPE)

This assay, run in 96 well flat-bottomed microplates, is used for the initial antiviral evaluation of all new test compounds. In this CPE inhibition test, four $log_{10}$ dilutions of each test compound (e.g. 1000, 100, 10, 1 µg/mL) are added to 3 wells containing the cell monolayer and within 5 minutes, the virus is added, the plate sealed, incubated at 37° C. CPE are read microscopically when untreated infected controls develop a 3 to 4+ CPE (approximately 72 to 120 hours). A known positive control drug is evaluated in parallel with test drugs in each assay run. Follow-up testing with compounds found active in initial screening tests are run in the same manner except 8 one-half $log_{10}$ dilutions of each compound are used in 4 wells containing the cell monolayer per dilution.

The data is expressed as 50% effective concentrations ($EC_{50}$).

Increase in Neutral Red Dye Uptake

This assay is run to validate the CPE inhibition observed in the initial test, and utilizes the same 96-well micro plates after the CPE has been evaluated. Neutral red is added to the medium; cells not damaged by virus take up a greater amount of dye, which is read on a computerized micro plate autoreader. The method as described by McManus (McManus, App Environ Microbiol, 1976. 31(1): 35-38) is used. An $EC_{50}$ is determined from the dye uptake.

BIT225 has antiviral activity against both amantadine sensitive and resistant viruses. Its broad-spectrum activity and in particular its activity against influenza B make it an important antiviral compound. The antiviral data against influenza A and B for BIT225 in Madin Darby canine kidney (MDCK) cells is summarized in Table 1. Commercially available antiviral agents generally do not have antiviral activity against influenza B.

TABLE 1

| Virus | Amantadine Sensitivity | Assay | $EC_{50}$ (µM) | $CC_{50}$ (µM) | SI | Comments |
|---|---|---|---|---|---|---|
| Influenza A (H1N1) | Sensitive | Neutral Red | 22 | 22 | 1 | Active |
| | | Visual | 4 | 32 | 8 | |
| Influenza A (H3N2) | Sensitive | Neutral Red | 2.2 | 45 | 20 | Active |
| | | Visual | 3.2 | 32 | 10 | |
| Influenza A (H5N1) | Resistant | Neutral Red | 3.2 | 15 | 4.5 | Active |
| | | Visual | 10 | 32 | 3.2 | |
| Influenza B | Resistant | Neutral Red | 3.6 | 17 | 4.7 | Active |
| | | Visual | 2.8 | 32 | 11 | |

Dose Response Plaque Reduction Assay

The anti-influenza A virus activity of BIT225 was confirmed by an in vitro dose response plaque reduction assay in Madin Darby canine kidney (MDCK) cells. The laboratory strain PR8 was used in these experiments and an amantadine resistant variant virus was made by mutating the M2 gene to encode sequence threonine at position 30 instead of alanine. The [A30T] mutant virus is known as PR8 4C.

The plaque assays were performed as described by Hayden et al. (Hayden et al., Antimicrob Agents Chemother, 1980. 17(5): 865-870) utilizing $1\times10^3$ pfu of the PR8 recombinant viruses in 150 µL of media to infect monolayers of MDCK cells.

This dilution of virus gives ~100 plaques in untreated control wells. BIT225 was dissolved in DMSO and added to media at the indicated final concentrations. Toxicity controls indicated no toxic effects of BIT225 up to 100 µM in MDCK cells.

FIG. 1 illustrates that BIT225 was able to reduce viral replication of both amantadine sensitive and resistant PR8 viruses. The $EC_{50}$ for BIT225 was approximately 10 µM against both the wild-type and A30T mutant viruses, with respective EC90 values of 12 µM and 18 µM. This is in stark contrast to the large shift in drug sensitivity to amantadine caused by the A30T mutation in M2.

Chimeric Virus Studies

Figure 2:
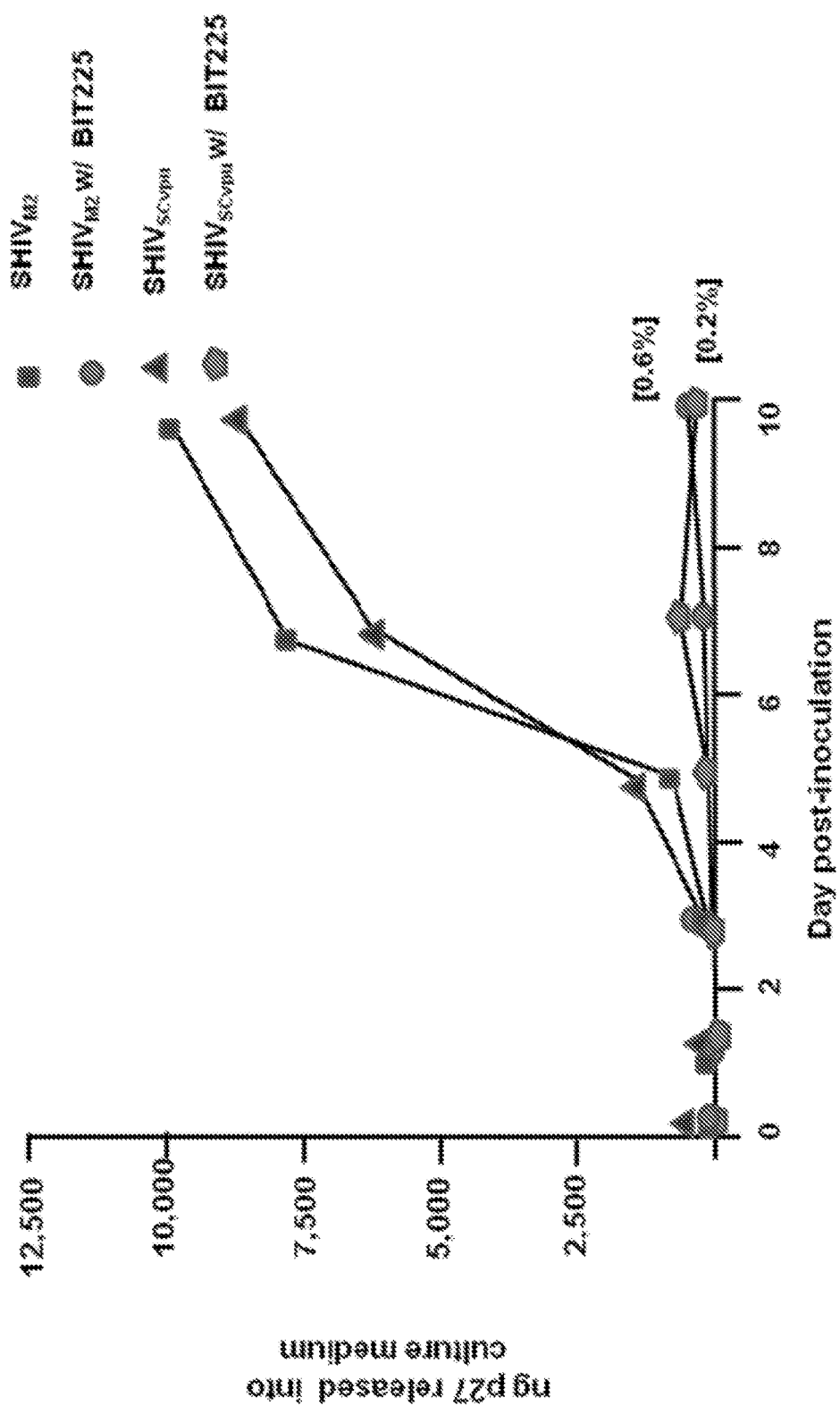
FIG. 2: This figure shows inhibition by BIT225 of replication in a T cell line (C8166) of the chimeric viruses SHIV-1$_{M2}$ and SHIV-1$_{SCVpu}$, which express the ion channel sequences of influenza A M2 or HIV-1 Vpu, respectively. Treatment with 10 µM BIT225 reduced virus released into the culture supernatant as measured by viral p27 protein. Controls treated with carrier solvent alone (DMSO) are shown for comparison

Experiments were conducted to examine the effect of BIT225 on replication in a T cell line (C8166) of the chimeric viruses SHIV-$1_{M2}$ and SHIV-$1_{SCVpu}$, which express the ion channel sequences of influenza A M2 or HIV-1 Vpu, respectively. Treatment with 10 µM BIT225 reduced virus released into the culture supernatant as measured by viral p27 protein (FIG. 2). Controls treated with carrier solvent alone (DMSO) are shown for comparison.

Figure 3:
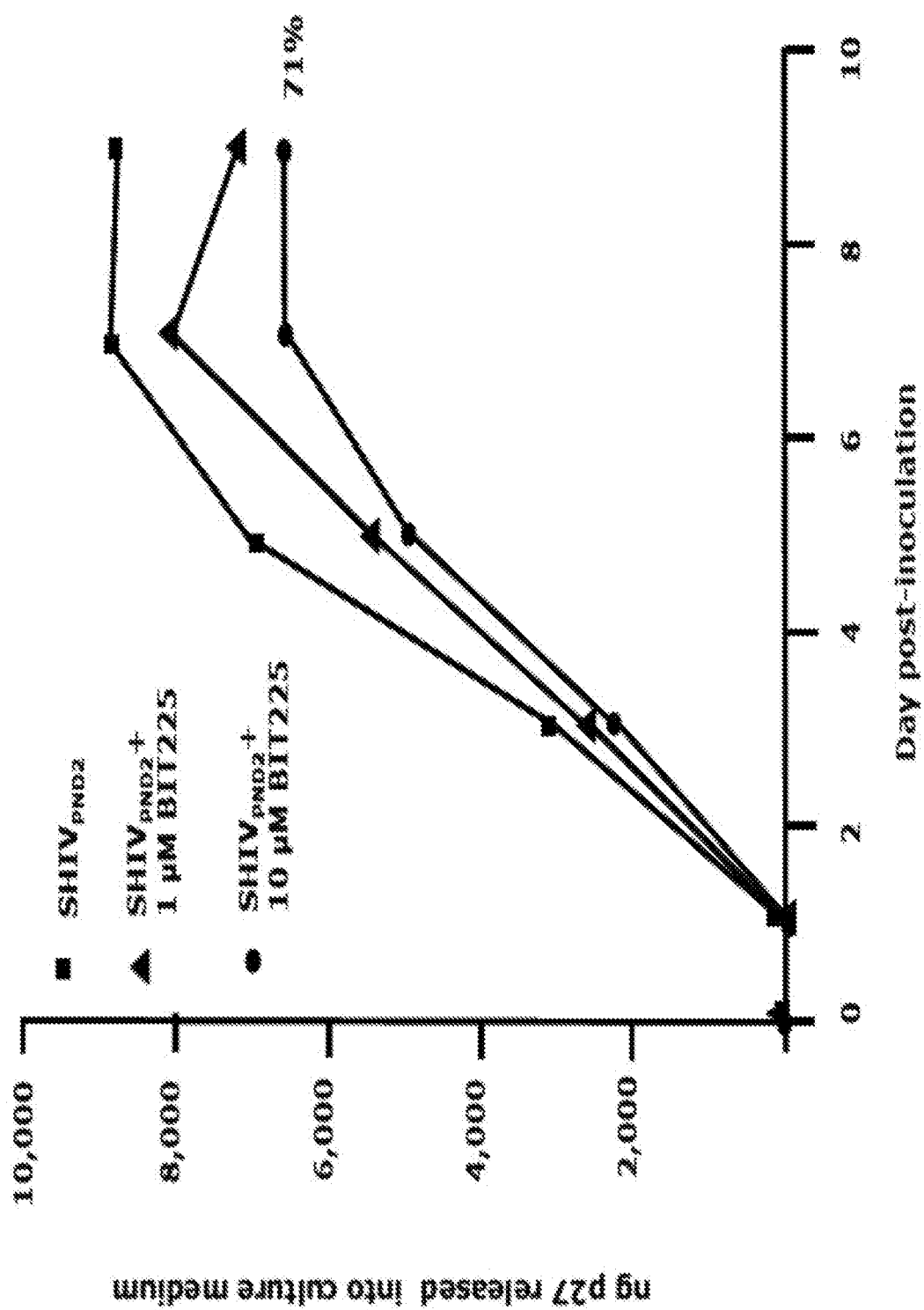
FIG. 3: This figure shows that treatment with 10 µM BIT225 of the mutant SHIV-1$_{PND2}$ virus with a non-functional Vpu ion channel does not significantly reduce virus replication.

However, treatment with 10 µM BIT225 of the mutant SHIV-$1_{PND2}$ virus with a non-functional Vpu ion channel does not significantly reduce virus replication (FIG. 3).

Taken together, these results indicate that inhibition of the Vpu or M2 ion channels is a possible mechanism of action of BIT225 for influenza.

The invention claimed is:

1. A method for inhibition of an influenza virus infection by the influenza virus in a subject, the method comprising administering to the subject an effective amount of N-carbamimidoyl-5-(1-methyl-iH-pyrazol-4-yl)-2-naphthamide, or a pharmaceutically acceptable salt thereof, wherein the administering inhibits replication of the influenza virus in the subject.

2. The method of claim 1, wherein severity, intensity, or duration of complications or symptoms associated with the infection by the influenza virus are reduced in the subject.

3. The method of claim 1, wherein titer of the influenza virus is reduced.

4. The method of claim 1, wherein the influenza virus is influenza A virus, influenza B virus or influenza C virus.

5. The method of claim 1, wherein the influenza virus is influenza A virus.

6. The method of claim 5 wherein the influenza A virus is H1N1, H1N2, H2N2, H3N2, H3N8, H5N1, H5N2, H5N3, H5N6, H5N8, H5N9, H7N1, H7N2, H7N3, H7N4, H7N7, H7N9, H9N2, or H10N7 subtype.

7. The method of claim 5, wherein the influenza A virus is H1N1, H3N2 or H5N1 subtype.

8. The method of claim 1, wherein the influenza virus is influenza B virus.

9. The method of claim 1, comprising administering the N-carbamimidoyl-5-(1-methyl-1H-pyrazol-4-yl)-2-naphthamide, or the pharmaceutically acceptable salt thereof, by an oral, nasal, intravenous, intraperitoneal, inhalation or topical route to the subject.

10. The method of claim 1, comprising orally administering the N-carbamimidoyl-5-(1-methyl-1H-pyrazol-4-yl)-2-naphthamide, or the pharmaceutically acceptable salt thereof, to the subject.

11. The method of claim 1, comprising administering a dosage of about 100 mg to about 600 mg of the N-carbamimidoyl-5-(1-methyl-1H-pyrazol-4-yl)-2-naphthamide, or the pharmaceutically acceptable salt thereof, to the subject.

12. The method of claim 1, comprising administering the N-carbamimidoyl-5-(1-methyl-1H-pyrazol-4-yl)-2-naphthamide, or the pharmaceutically acceptable salt thereof, orally, once daily at a dosage of about 100 mg to about 200 mg, to the subject.

13. The method of claim 1, comprising administering the-N-carbamimidoyl-5-(1-methyl-1H-pyrazol-4-yl)-2- naphthamide, or the pharmaceutically acceptable salt thereof, orally, twice daily at a dosage of about 100 mg to about 200 mg, to the subject.

14. The method of claim 1, comprising administering the N-carbamimidoyl-5-(1-methyl-1H-pyrazol-4-yl)-2-naphthamide, or the pharmaceutically acceptable salt thereof, in combination with one or more additional antiviral agents, to the subject.

15. The method of claim 14, wherein the one or more additional antiviral agents comprises zanamivir, oseltamivir and/or peramivir.

\* \* \* \* \*